United States Patent
Rubin

(10) Patent No.: US 11,395,840 B2
(45) Date of Patent: Jul. 26, 2022

(54) ENHANCED HERB OR FOOD PRODUCT AND METHOD

(71) Applicant: GRV Fund, LLC, Jupiter, FL (US)

(72) Inventor: Jordan Seth Rubin, Koshkonong, MO (US)

(73) Assignee: BYO Holdings, LLC, Koshkonong, MO (US)

( * ) Notice: Subject to any disclaimer, the term of this patent is extended or adjusted under 35 U.S.C. 154(b) by 108 days.

(21) Appl. No.: 16/270,033

(22) Filed: Feb. 7, 2019

(65) Prior Publication Data

US 2019/0307824 A1 Oct. 10, 2019

Related U.S. Application Data

(63) Continuation of application No. 15/204,280, filed on Jul. 7, 2016, now abandoned.

(60) Provisional application No. 62/190,039, filed on Jul. 8, 2015.

(51) Int. Cl.

| | |
|---|---|
| *A61K 36/00* | (2006.01) |
| *A61K 36/185* | (2006.01) |
| *A23L 25/00* | (2016.01) |
| *A23L 19/00* | (2016.01) |
| *A61K 9/00* | (2006.01) |

(52) U.S. Cl.
CPC ............ *A61K 36/185* (2013.01); *A23L 19/00* (2016.08); *A23L 25/00* (2016.08); *A61K 9/0053* (2013.01); *A61K 2236/51* (2013.01)

(58) Field of Classification Search
CPC .................................................. A61K 2236/51
See application file for complete search history.

(56) References Cited

FOREIGN PATENT DOCUMENTS

| | | | |
|---|---|---|---|
| CN | 103191234 A | * | 7/2013 |
| CN | 103933535 A | * | 7/2014 |
| KR | 1396807 B1 | * | 5/2014 |

OTHER PUBLICATIONS

Pickens, Sedative activity of cannabis in relation to its delta'-trans-tetrahydrocannabinol and cannabidiol content. British journal of pharmacology, (Apr. 1981) vol. 72, No. 4, pp. 649-656 (Year: 1981).*

* cited by examiner

*Primary Examiner* — Qiuwen Mi
(74) *Attorney, Agent, or Firm* — Barbara E. Johnson, Esq.

(57) ABSTRACT

The present invention is a method of preparing and potentiating functional foods and, in particular, herbs, by subjecting the food or herb to specific method steps, either a particular three- or four- step potentiating process or a specific infusion/fermentation potentiating technique, for which in some embodiments the fermentation is optional.

2 Claims, No Drawings

ENHANCED HERB OR FOOD PRODUCT
AND METHOD

CROSS-REFERENCE TO RELATED
APPLICATIONS

This patent application claims priority to, and incorporates herein by reference, U.S. Provisional Patent Application No. 62/190,039, "Enhanced Herb or Food Product and Method," filed 8 Jul. 2015, and furthermore is a continuation of U.S. patent application Ser. No. 15/204,280 filed 7 Jul. 2016, also incorporated herein by reference.

BACKGROUND OF THE INVENTION

Field of the Invention

The invention pertains to methods of enhancing and potentiating herbs or (primarily functional) foods by ecologically friendly treatments with natural, whole food agents.

Description of Related Art

There is no question that up-to-date notions of nutrition appreciate, and often demand, nutrient-rich substances which were common among indigenous cultures in the last century and in more remote areas today. Even the existence of a resource such as the *Handbook of Nutraceuticals and Functional Foods* (Robert E. C. Wildman, ed., CRC Press, Taylor & Francis Group, LLC, Boca Raton, Fla., 2007) speaks volumes about the demand for dietary sources that go beyond simple nutrients to health and wellness enhancers that often seem more like medicaments than foods. Functional food approaches, such as homemade combinations of various aromatics that gain a following as "natural antibiotics," are no longer peripheral or fad practices but are increasingly appreciated in many households chiefly because they truly work to ward off illnesses such as the common cold or flu. Herbs, in particular, may have been the province of Traditional Chinese Herbal Medicine in prior decades, but herbal products and remedies are so common at this writing that they can be purchased either at the most elite natural foods establishments or at the most basic of discount retail stores throughout the United States and elsewhere.

Particularly as herbal products become more widely available, challenges involved in manufacture, storage, delivery and shelf life are critical to a ensure a high quality effective product. Whole herbs dried and delivered in capsules lack efficacy as the dosage of active ingredients is simply too low and absorption potential is inefficient. Heat liable compounds are susceptible to oxidation if the drying proceeds at too high a temperature or, conversely, to various sorts of degradation if the drying process is insufficient. At the same time, extracts of herbs have presented new and different challenges compared to dried whole herb products. An extract which concentrates for one compound (say, an extraction of Turmeric for the compound of curcumin) may be high in the desired curcumin compound but will have by definition eliminated other known or not-yet-known desirable compounds or compositions in the turmeric as a result of the extraction. As an example, if turmeric contains 3% curcumin, an extract of curcumin from turmeric will render at least 97% of the turmeric as waste product when, even intuitively, one can appreciate that there exists other nutritional value in the remaining 97% of the turmeric. Common herbal extractions may introduce undesirable solvents such as hexane which introduces a toxin into both the product and the environment. Perhaps the most common solvent in used in liquid herbal extracts is alcohol/ethanol which is not ideal for certain customers who abstain from any alcohol consumption. This challenge is much more than one of manufacturing efficiency: consumers of today routinely demand a "whole food or whole herb" approach to dietary supplementation and know that, for example, Vitamin C is best taken with its customarily-accompanying bioflavanoids, and thus generally understand and demand that medicaments or functional foods contain multiple active agents derived from their natural sources and maintained in active mixture together. Accordingly, a need remains for highly potentiated food or herbal products for human and animal consumption which avoid most or all of the problems associated with traditional unprocessed dried whole herbs and herbal extracts of the prior art.

SUMMARY OF THE INVENTION

In order to meet this need, the present invention is a method of preparing and potentiating functional foods and, in particular, herbs, by subjecting the food or herb to specific method steps, either a particular four step potentiating process or an infusion/fermentation potentiating technique. Each of these methods importantly involves fermenting the herb or food material as part of the inventive processing. The first of the two particular processes requires all of the following steps. First, the food or herb is soaked in a fruit-, vegetable-, seed- or grain-based naturally acidified liquid, preferably but not limited to a raw, unpasteurized organic vinegar, for between 3 and 14 day at 68-90 degrees F., to liberate the minerals contained in the herb together with a portion of the alcohol soluble fraction of herb or food (acted upon by the small amount-less than 1%-of alcohol present in some such liquids). Second, the resulting herbal material and soaking liquid, still in admixture, is (optionally, but preferably) steamed at 250 degrees F. for between 4 and 12 hours to soften the substrate and to liberate the water-soluble phytonutrients without denaturing them, similar to a traditional herbal decoction. Third, the previously steamed substrate, still containing the initial soaking liquid, is fermented together with an added amount of raw, unpasteurized vinegar and starter culture, "the mother," capable of serving as a fermentation inoculum for 3-14 days at a temperature of 68-90 degrees F., preferably at about 78 degrees F. Finally, the fermented materials including all the solids and liquids are dried at low temperature, raising the temperature of the substrate to a maximum of 118 degrees F., whether internal, surface temperature or liquid temperature, by using one of the following methods: freeze drying, air drying, spray drying or vacuum dehydration. In the second method, the food or herb may be fermented and, either prior to or during fermentation, one or more essential oils or supercritical $CO_2$ oils or extracts are infused into the native food or herb, so that the fermentation acts on the native material and the infused essential oil(s) or extract(s) all together, prior to careful drying, powdering and inclusion in an oral nutraceutical dosage form. The single or combination of food and/or herb that results from either of the above treatment methods is a nutritionally enhanced substrate which has the benefit of an additional intrinsic presence of acid-loving bacteria such as without limitation *Acetobacter* as well as desirable naturally created organic acid constituents such as malic acid, acetic acid, gluconic acid and succinic acid. The resulting product also constitutes the best of both a whole, dried herb or food and an extracted herb or food, without being (or experiencing the detriments) of either a traditionally dried whole herb or an extract per the prior art.

DETAILED DESCRIPTION OF THE INVENTION

In order to achieve the above-described results of the disclosed inventive method, some additional explanation and disclosure is illustrative.

Both methods of the present invention are effective to potentiate a wide variety of functional foods and herbs and the potential nutritional or functional substrates are really without limit (presuming they are otherwise wholesome and potable, etc.). Having said that, certain botanicals are particularly well suited to the practice of the invention and these include, without limitation, Kidney Bean; Pumpkin Seed; Fava Bean; Chia Seed; Green Split Pea; Flax Seed; Green Lentil; Garbanzo Bean; Hemp Seed; Black Bean; Mung Bean; Adzuki Bean; Sesame Seed; Cranberry Bean; Great Northern Bean; Lima Bean; Navy Bean; Pinto Bean; Black rice; Ashwaghandha; Atractylodes, Gynostemma, Cacao; Purple Millet, Black Quinoa, Red Quinoa, Red Canihua, Cannabis Sativa/Indica flowers or leaves; Spirulina; Lemon Peel; Anise; Star Anise; Chili Pepper; Kelp; Alfalfa leaf; Watercress; Cilantro; Sage; Seabuckthorn; Thyme; Parsley; Broccoli Seed; Mate; green Coffee Beans; Roasted Coffee Beans; Green Tea; Rhodiola; Siberian Ginseng; Sea Buckthorn Berry; Black Soy Bean; Olive leaf; Cabbage; Milk Thistle seed; Milk Thistle leaf; Turmeric; Bupleurum; Artichoke leaf; Dandelion leaf; Dandelion root; Hibiscus flower; Vanilla Seed; Ginkgo leaf; Bacopa; Periwinkle; Peppermint; Hawthorn Berry; Cardamon; Garlic; Mung Bean; Astragalus Root; *Echinacea purpurea* root; *Echinacea augustifolia* root; *Echinacea augustifolia* leaf; Elder berries; Elder Flower; Goldenseal Leaf; Goldenseal root; Olive Leaf; Ginger; Carrot; Orange Peel and Blossom; Grapefruit Peel and Blossom; Ajowain Fruit; Allspice; Clove; Cinammon; Fennel; Kelp; Bitter Orange/Bergamot; Hibiscus Flower; Frankincense tears; Holy Basil; Arnica; Celery seed; Balm Leaf; Bilberry leaf; *Gymnema sylvestre* leaf; Fenugreek; Galangal; Bitter Melon; Cumin; Black Cumin; Primrose; Evening Primrose; Borage Seed; Cardamom; Saw Palmetto; Nettle; Red Clover Blossom; Black Cohosh; Chaste Tree Berries; Dong Quai Root; Hop Flowers; Licorice root; Wild Yam; Thyme Leaf; Oregano; Hyssop; Marjoram; American Ginseng; Panax Ginseng—red and white; Cruciferous vegetables; Schizandra; Goji Berry; Tribulus; Velvet Bean; Cranberry; Almonds; Epimidium; Sigsbeckia orientalis; Shilijit (note this is a mineral, not an herb); Noni Fruit; Grapeseed-skin, -leaf and -stem; Asarum Sieboldii; Mulberry leaf and root; Kudzu vine; Isatis tinctoria; Scuttelaria barbara; Scuttelaria Baicalensis; Phellodendron amurense; Lyciium chinense; Angelica pubescens; Clerodendrum trichotomum; Codonopsis tangshen; Dioscorea opposita; Cistanche salsa; Polygonum multiflorum; Caraluma fimbriata; Ashitaba; Moringa leaf; Tart Cherry; Camu Camu; Salacia oblonga; Lavender; Clary Sage; Cedarwood; Marigold; Tea Tree; Eucalyptus; Nutmeg; Lemon Myrtle; Rosemary; Chamomile; Roman Chamomile; Geranium; Geranium Rose; Lemongrass; Vetiver; Paprika; Pomegranate and Coriander.

In the above-mentioned four step process of the invention, a substance selected from the previous paragraph—or another functional food or herbal material—is first subjected to a liquid acidic potentiation within the following limits. The potentiation liquid should be a fruit-, vegetable-, seed-, or grain-derived acidic medium, preferably vinegar, having an acid content of between 3-15 percent by weight, preferably 4-8 percent by weight of water. By "vinegar" is meant an acetic acid solution in a substantially water base. Other acidic liquids are acceptable for this step and can include, without limitation, liquids rich in citric acid, malic acid, gluconic acid and succinic acid such as lemon juice. The amount of liquid solution to use is not critical, but enough liquid should be used to cover completely the food or botanical to be potentiated. A 3-14 day soaking should then be allowed to proceed, preferably with little or no stirring, shaking or disturbance of the material in the liquid, under room temperature conditions as described above. After the 3-14 days, the substrate (material plus liquid) is steamed at 250 degrees F. for 4-12 hours. By "steamed at 250 degrees F." is meant a steaming protocol wherein the substrate's fermentation vessel is surrounded by steam creating an "herbal decoction" within the substrate including soaking liquid wherein the steam itself raises the internal temperature of the substrate above boiling, i.e. 212-250 degrees F. Although the steaming step is optional, the preferred embodiment of the invention includes the steaming protocol. As a third step, the previously treated and optionally steamed substrate (with all its initial soaking and steaming liquids still intact) is inoculated with a new solution containing raw, unpasteurized vinegar having an acid content between about 4 and 8 percent containing the live fermenting culture "mother". This raw, unpasteurized vinegar should be of a type suitable to use as a fermentation inoculum containing *Acetobacter* or other popular or conventional food fermentation bacteria—therefore, in this step, vinegar specifically should be used and not some other form of acid rich food. Fermentation should be allowed to proceed at a temperature between 68 and 90 degrees F., preferably at about 78 degrees F.

After the above three steps are complete, the resulting food, herb or combination thereof is gently dried. Low temperature drying techniques can be selected from among one or of freeze drying, vacuum dehydration, air drying or spray drying. The maximum temperature that the drained food or herb should be allowed to attain is 118 degrees F.; preferably, drying proceeds at temperatures of 105-110 degrees F.

The second method of the invention has some similarities to the above first-describe four step process, but with a different emphasis and outcome. A food or herb selected from the list above (or another one, without limitation) is fermented, using a fermenting agent. For the purpose of this second fermentation method, the microbial agent need not be a bacterium but can be any of among bacteria, yeasts, molds, algae, animal cells, or plant cells as long as each is edible and safe and each is suitable to fermentation of a product intended for ingestion or other administration. Of these agents, bacteria and fungi (including yeasts) are preferred. Either before or during the fermentation, the same or a different essential oil (or supercritical $CO_2$ extract) as is present in the food or herb innately is infused into the food or herb (or a multiple of essential oils or extracts) so that the fermentation acts both on the native constituents of the food or herb and also on the infused added one or more essential oils or extracts. So, for example, peppermint leaf can be infused with peppermint essential oil prior to fermentation; cannabis herb starting material can be infused with cannabidiol extract prior to fermentation, lavender leaves can be infused with lavender essential oil prior to fermentation, and so forth. Alternatively, orange peel (by way of nonlimited example) can be infused with Curcumin extract, Cannabis sativa leaves can be infused with Lavender essential oil, and so on, but the inventive key here is that the starting food or herb is infused with at least one additional essential oil or extract of another food or herb, prior to or during fermentation.

The second method of this patent application may literally be practiced with any starting food or herb and any infused oil or extract, as discussed above. By way of example, and without limitation, the essential oils or extracts could be any of the essential oils or extracts available from commercial sources commonly available in the marketplace. A typical list of essential oils or extracts available from such a source could include, without any limitation, Allspice, Amyris, Angelica Root, Arborvitae, Basil, Bergamot, Birch, Black Pepper, Blood Orange, Blue Tansy, Buddha Wood, Cajeput, Camphor, Cananga, Caraway, Cardamom, Carrot Seed, Cassia, Cedarwood Atlas, Cedarwood Himalayan, Celery Seed, Chamomile German, Chamomile Roman, Cilantro, Cinnamon Bark, Cinnamon Leaf, Cistus, Citronella, Clary Sage, Clementine, Clove, Cocoa, Coffee, Cognac, Copaiba, Coriander, Cumin, Cypress, Cypriol, Davana, Dill Weed, Elemi, Eucalyptus Globulus, Eucalyptus Radiata, Fennel, Fir Balsam, Fir Needle, Frankincense Carterii, Frankincense Serrata, Galbanum, Geranium, Ginger, Goldenrod, Grapefruit, Helichrysum Italicum, Helichrysum Splendidum, Hyssop, Jasmine, Juniper Berry, Key Lime, Laurel Leaf, Lavender, Ledum, Lemon, Lemongrass, Lime, Litsea, Mandarin, Melissa, Mountain Savory, Muhuhu, Myrhh, Myrtle, Neroli, Nerolina, Niaouli, Nutmeg, Opoponax, Oregano, Palmarosa, Palo Santo, Parsley, Patchouli, Peppermint, Peru Balsam, Petitgrain, Pine, Plai, Ravensara, Ravintsara, Rose Bulgarian Absolute, Rose Geranium, Rose Moroccan Absolute, Rosemary Moroccan, Rosemary Spanish, Rosewood, Sage, Sandalwood Australian, Sandalwood East Indian, Spearmint, Spikenard, Spruce, Sweet Marjoram, Sweet Orange, Tagetes, Tangerine, Tarragon, Tea Tree, Thyme, Turmeric, Valerian, Vanilla, Verbena, Vetiver, White Fir, Wild Orange, Wintergreen, Yarrow and Ylang Ylang.

Typically, the fermentations of this second inventive method are not conducted with any heating or steaming, because the low (ambient or slightly elevated) temperature fermentation and concomitant low temperature drying maximizes the preservation of biologically active compounds, acids and enzymes both in the fermentation mixture and in the carefully dried and gently powdered end product.

Without being limited by the following list, suitable fermentation agents (microorganisms) can be selected from the group consisting of *Acetobacter, Arthrobacter, Aspergillus, Bacillus, Bifidobacterium, Brachybacterium, Brevibacterium*, Candida, *Carnobacterium, Corynebacterium*, Cyberlindnera, Debaryomyces, *Enterococcus, Gluconacetobacter, Lactobacillus*, Leuconostoc, *Microbacterium, Pediococcus*, Penicillium, Pichia, *Propionibacterium, Saccharomyces, Staphylococcus, Streptococcus, Tetragenococcus*, Verticillium, *Weissella*, Yarowia, Zygotorulaspora and *Zymomonas*. Any microorganism known now or hereafter developed is suitable for use in the present invention.

Quantities for use in practicing the second method of this invention can vary, but as a general rule the added essential oil or extract is infused into the food or herbal starting material so that it will constitute about 0.05-5% of the dry weight of the resulting blend in its final, comminuted or powdered form. So, for example, 100 g. of fresh peppermint leaves may be, for example, infused with 2 g of peppermint essential oil before or during the fermentation of the peppermint leaves with at least one microorganism, under standard culinary fermentation conditions, as a way of practicing the second method of the present invention. Similarly, 100 g of fresh Cannibis sativa can be infused with about 1 g of cannabidiol before or during fermentation of the Cannabis leaves (or flowers, stems, stalks or roots). The inventor believes that part of the beneficial result of the second method disclosed herein, specifically in the manufacturer of highly active nutraceutical compositions, involves the broadest possible fermentation spectrum of biologically active compounds, as the fermentation acts on both the native food or herbal material and the infused material, and the chemical results of fermentation are slightly-to-significantly different for these two fermentation substrates. In particular, infusing the infusing oil or extract into the "whole" herb or food is preferred for this very reason—the widest possible panoply of resulting active agents, resulting from the fermentation, will occur if the largely or completely intact leaf, seed, bean, etc. is infused with the infusing agent prior to or during fermentation. (In other words, the second process of the invention is quite far away, conceptually, from known culinary methods for making tofu or yogurt products.) For both methods of the invention, fermentation conditions are those known in the art—as to temperature, humidity, length, etc. Also for both methods, drying and powdering should be at low temperature, and using gentle mechanics and pressures. Therefore, if fermentations proceed at between 68 and 90 degrees F., preferably 78 degrees F., then subsequent drying and powdering should occur at no higher than 118 degrees F., and preferably no higher than about 105-110 degrees F. Powdering of dried material should take place gently, which is to say without any more than trivial heat of friction as a result of the powdering method chosen. Heat-avoiding powdering techniques for foodstuffs and nutraceuticals containing active enzymes and biological compounds are known in the art and include freeze drying air drying, spray drying and vacuum dehydration.

Notwithstanding all of the above, a particular embodiment of the invention pertains to infused Cannabis leaves or plant parts (whole leaves, flowers, stems, stalks or roots, or minimally divided leaves, flowers, stems, stalks or roots, that is, not dried or cominuted) that are infused with one or more essential oils or extracts known to stimulate the Endocannabinoid System (ECS) of the human body upon oral administration. The combined Cannabis leaves, flowers, stems, stalks or roots and the added one or more essential oils or extracts may be fermented, or may be dried and formulated into an oral dosage form without fermentation during or after combination. Not all essential oils or extracts stimulate the ECS, but for those that do, the infusion with Cannabis whole (mostly whole) leaves, flowers, stems, stalks or roots, prior to dehydration and powdering give new and unexpected results compared to administration of either the dried and powdered Cannabis leaves, flowers, stems, stalks or roots by themselves, orally, or the essential oil(s) or extract(s), orally, one without the other. It is believed that the infusion of the one or more essential oils or extracts into the Cannabis native leaf, flower, stem, stalk or root material gives rise to a panel of constituents which stimulate the ECS in a synergistic way, compared to the narrower availability of multiple ECS stimulating agents in either the leaves (or stalks, roots, flowers or stems) or the additives alone. The essential oils (pressed or distilled) or extracts, including carbon dioxide extracts, that are suitable for this embodiment of the invention and for combination with Cannabis are selected from the group consisting of Artemesia, Camellia, Cannabis, Catha, Desmodium, Echinacea, Glycine, Helichrysum, Heliopsis, Laminaria, Lepidium, Lyngbya, Morinda, Pinus, Piper, Pistacia, Protium, Radula, Rhodiola, Ruta, Salvia, Syzygium, Trifolium, and Turmeric (Curcurmin). In addition to the believed synergistic effect of oral administration of combined Cannabis and an essential oil or extract from the list above, there are also modulating effects of co-administration including, but not limited to, reduction of unwanted side effects from, for example, the tetrahydrocannabinol (THC) and even the cannabidiol (CDB) constituents of either the Cannabis or the oil or extract, in that the combined active agent(s) amplify the good effects and reduce the unwanted side effects. So, for example, when curcurmin (turmeric) essential oil or extract is added to Cannabis and the resulting combination is carefully dried and powdered for oral administration, the curcurmin modulates the unwanted psychoactive effects of the THC—when the oral dosage form is administered for pain relief—without reducing the pain relieving action of either the THC or the CBD. Although fermentation of the combination does amplify even further the myriad of active agents present in the combination of Cannabis with at least one of the above listed essential oils or extracts, in the particular case of Cannabis described in this paragraph, fermentation is optional. As with the other embodiments of the present invention that include an infused oil or extract, an amount of oil or extract should be used to comprise about 0.5-5% by weight of the final weight of the dried and powdered product.

Although the invention has been described in connection with particulars, above, and enumerated constituents and method parameters, the invention is only to be limited insofar as is set forth in the accompanying claims.

I claim:

1. A method for stimulating or modulating the endocannabinoid system of a patient consisting of the steps of infusing Cannabis whole or minimally divided leaves, stems, flowers, stalks, or roots that are neither dried nor cominuted with at least one essential oil or extract which is known to stimulate or to modulate the endocannabinoid system, said essential oil or extract being selected from the group consisting of Artemesia, Camellia, Cannabis, Catha, Desmodium, Echinacea, Glycine, Helichrysum, Heliopsis, Laminaria, Lepidium, Lyngbya, Morinda, Pinus, Piper, Pistacia, Protium, Radula, Rhodiola, Ruta, Salvia, Syzygium, Trifolium, and Turmeric, to create an infused Cannabis material, drying and powdering said infused Cannabis material to create an oral dosage form, and administering said oral dosage form to a patient in whom endocannabinoid stimulation or modulation is indicated.

2. A method for stimulating or modulating the endocannabinoid system of a patient consisting of the steps of infusing Cannabis whole or minimally divided leaves, stems, flowers, stalks, or roots that are neither dried nor cominuted with at least one essential oil or extract which is known to stimulate or to modulate the endocannabinoid system, said essential oil or extract being selected from the group consisting of Artemesia, Camellia, Cannabis, Catha, Desmodium, Echinacea, Glycine, Helichrysum, Heliopsis, Laminaria, Lepidium, Lyngbya, Morinda, Pinus, Piper, Pistacia, Protium, Radula, Rhodiola, Ruta, Salvia, Syzygium, Trifolium, and Turmeric, to create an infused Cannabis material, subsequently fermenting without heating or steaming said Cannabis material, and drying and powdering said infused Cannabis material to create an oral dosage form, and administering said oral dosage form to a patient in whom endocannabinoid stimulation or modulation is indicated.

* * * * *